United States Patent

Guo et al.

[11] Patent Number: 5,911,165
[45] Date of Patent: Jun. 8, 1999

[54] METHOD AND DEVICE FOR MECHANICAL TESTING OF FIBRIN GLUE STRENGTH

[75] Inventors: John W. Guo, El Cerrito; Rajiv Nayar, Richmond, both of Calif.

[73] Assignee: Bayer Corporation, Berkeley, Calif.

[21] Appl. No.: 08/864,797

[22] Filed: May 29, 1997

[51] Int. Cl.$^6$ .................................................. G01N 3/24
[52] U.S. Cl. ...................................... 73/827; 73/842
[58] Field of Search ........................... 73/826, 827, 841, 73/842, 846

[56] References Cited

U.S. PATENT DOCUMENTS

| | | | |
|---|---|---|---|
| 4,909,251 | 3/1990 | Seelich | 424/101 |
| 4,957,044 | 9/1990 | McKinlay et al. | 73/842 |
| 5,176,028 | 1/1993 | Humphrey | 73/842 |
| 5,476,509 | 12/1995 | Keogh et al. | 623/1 |
| 5,651,982 | 7/1997 | Marx | 424/450 |

*Primary Examiner*—Max H. Noori
*Attorney, Agent, or Firm*—Michael J. Beck; James A. Giblin

[57] ABSTRACT

An improved method and device for measuring the mechanical properties of fibrin clots. A mixture of fibrinogen and thrombin is formed between two synthetic polymeric substrate materials and allowed to form a fibrin clot. The force required to separate the substrate materials is then measured and indicates the strength of the clot.

2 Claims, 5 Drawing Sheets

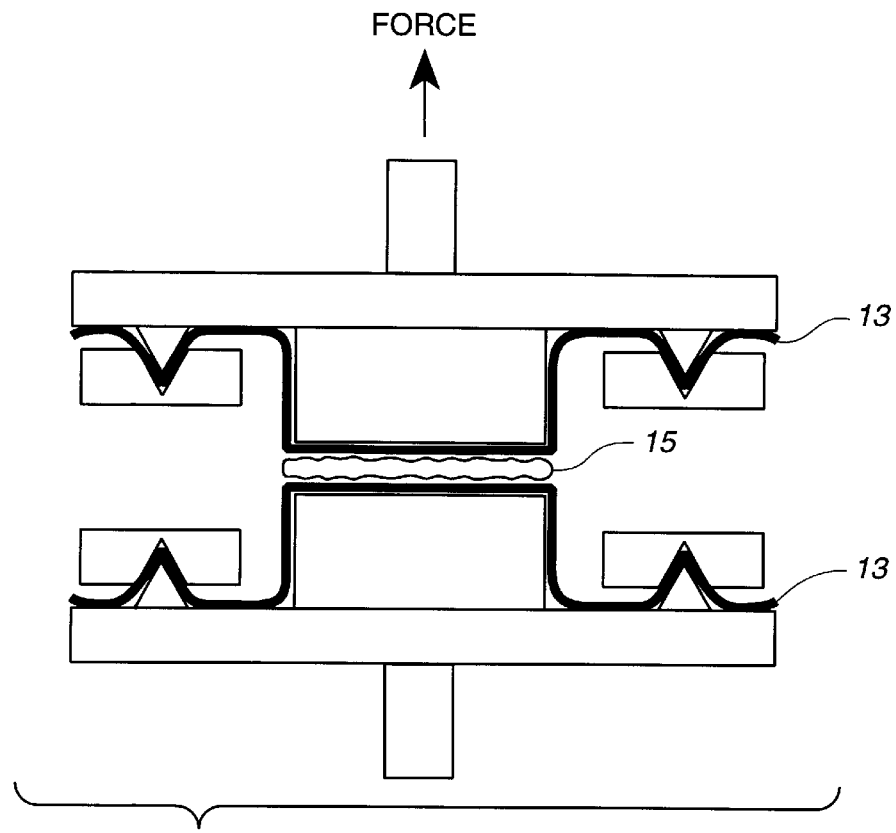
FIG._1
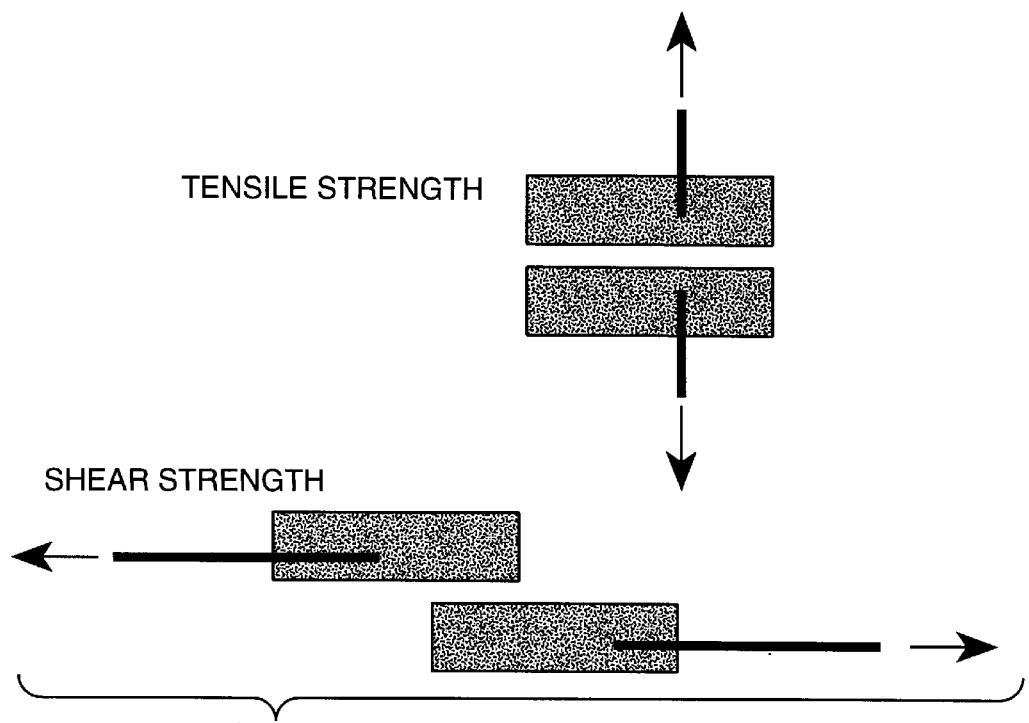
FIG._2

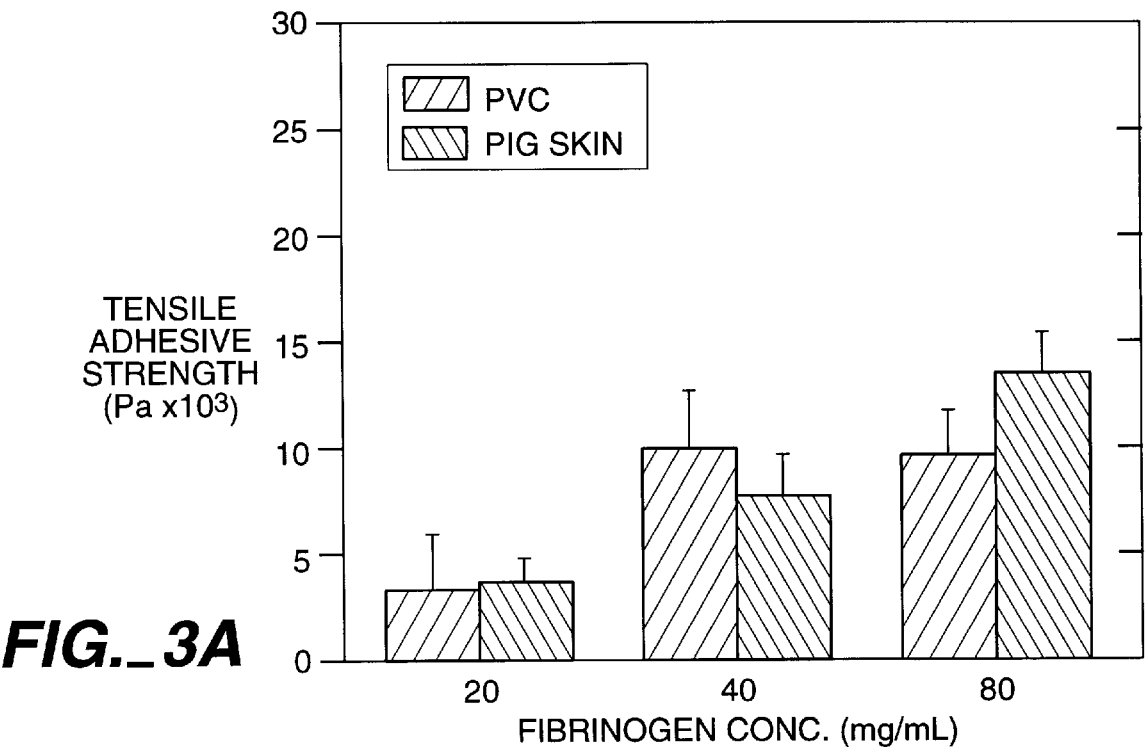
FIG._3A
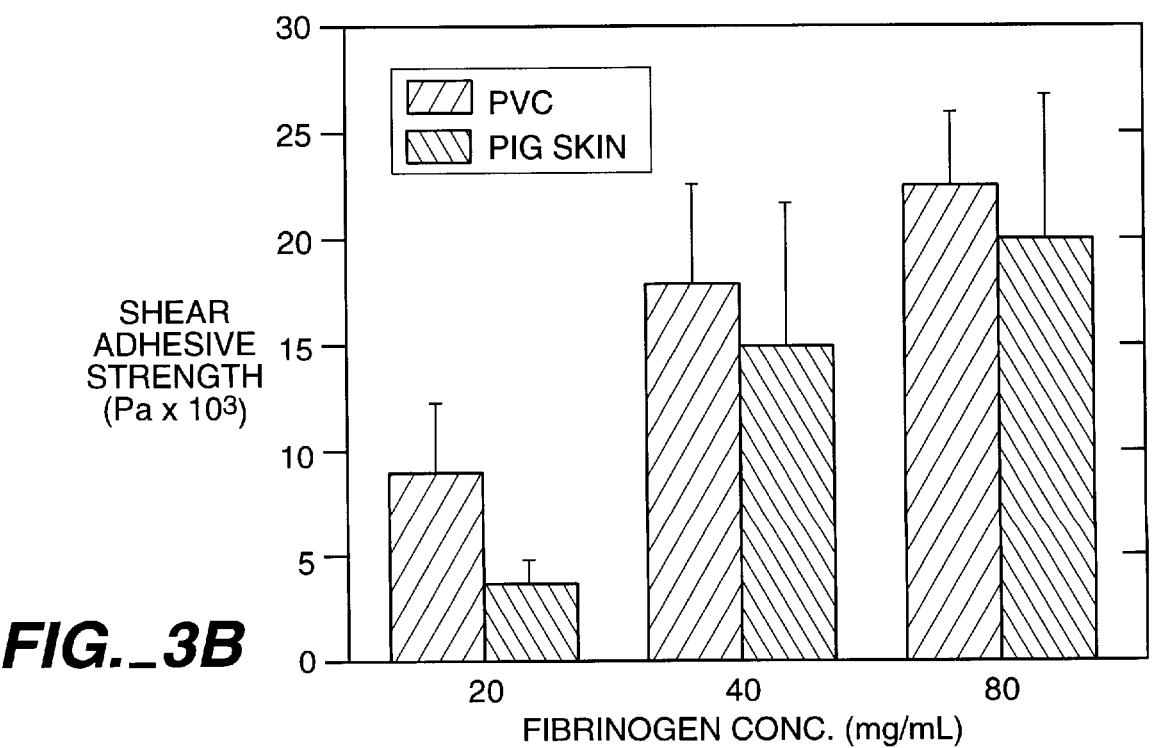
FIG._3B

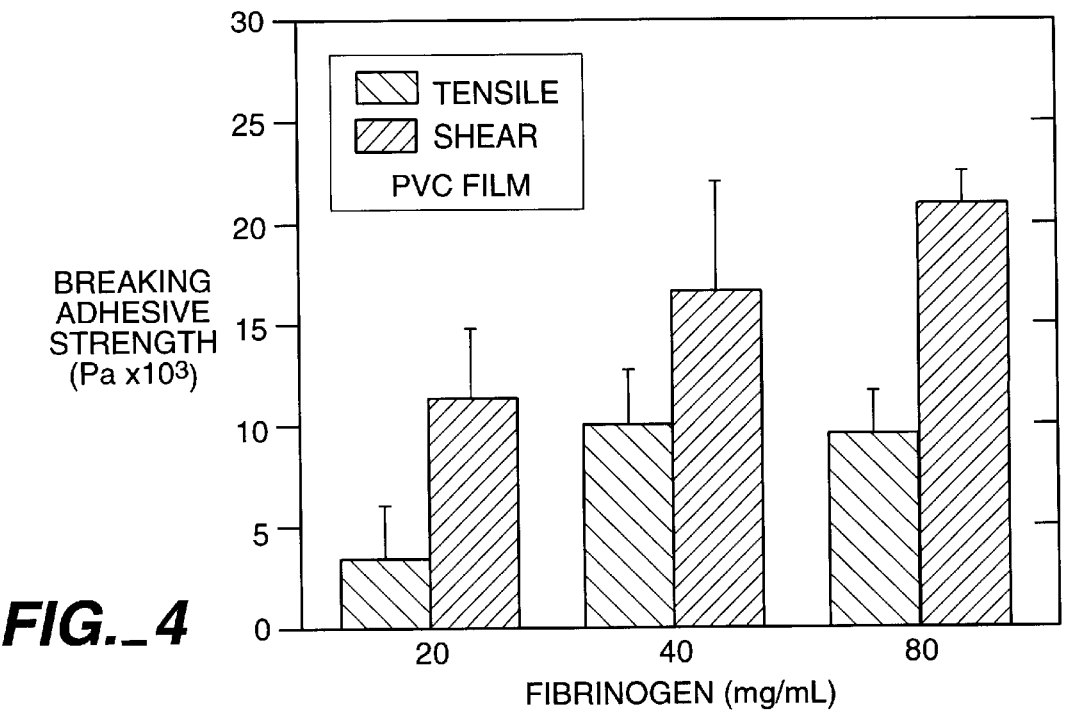
FIG._4
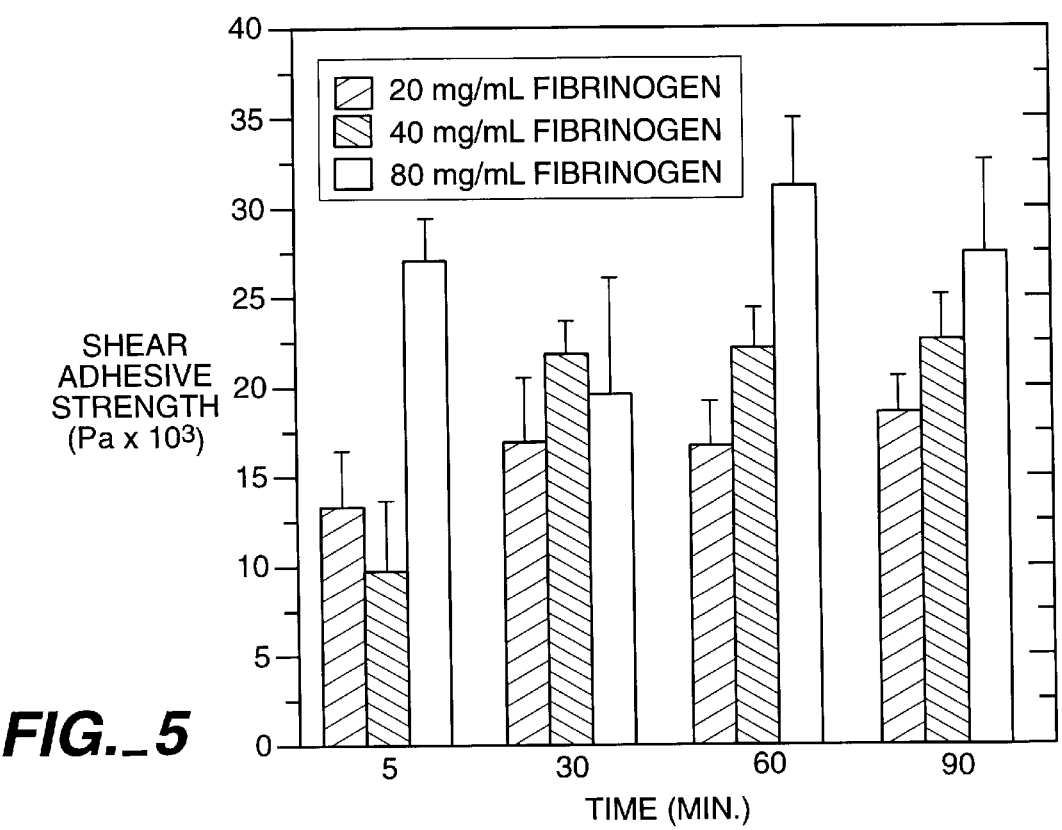
FIG._5

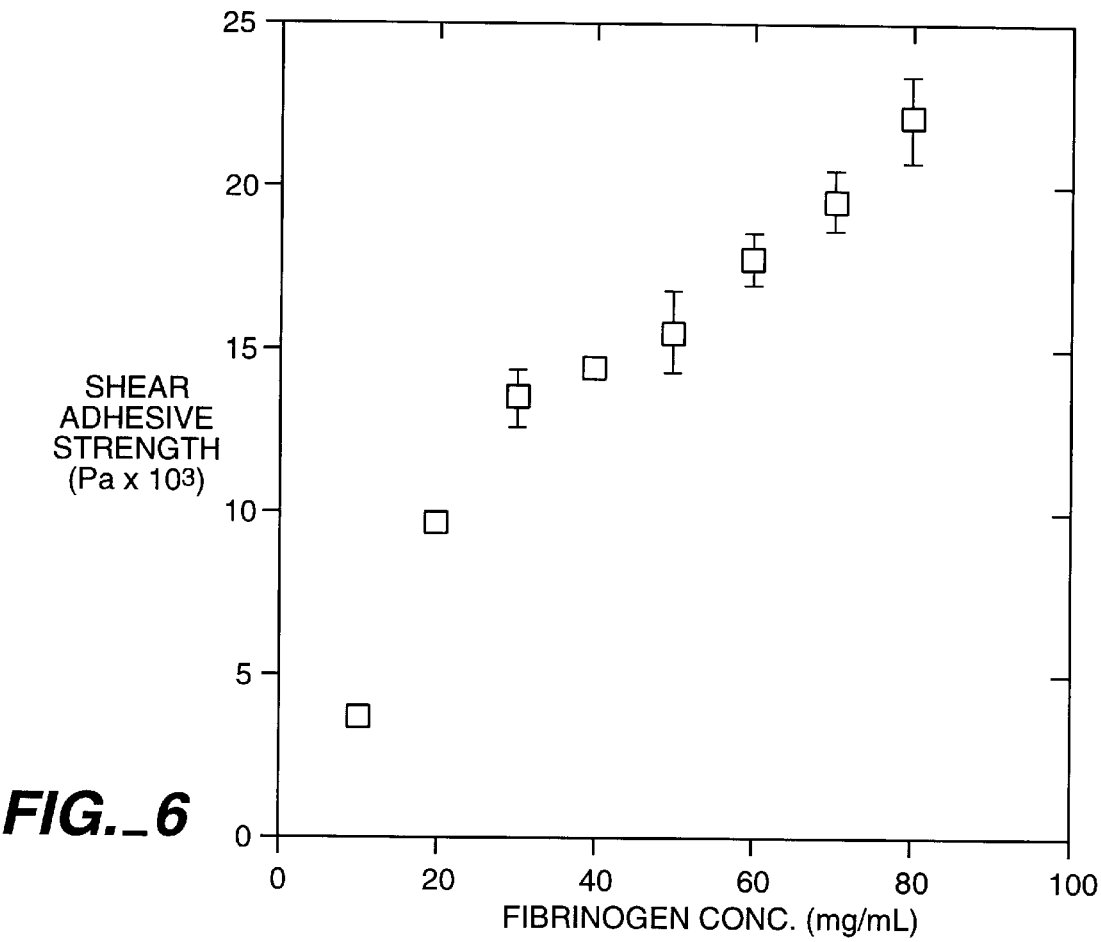
FIG._6
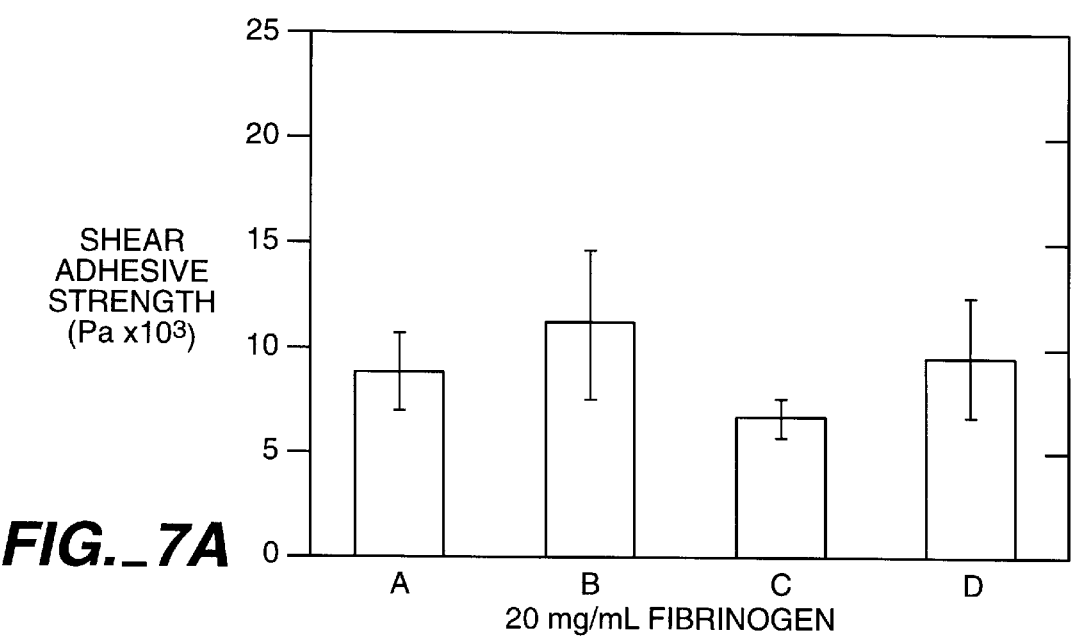
FIG._7A

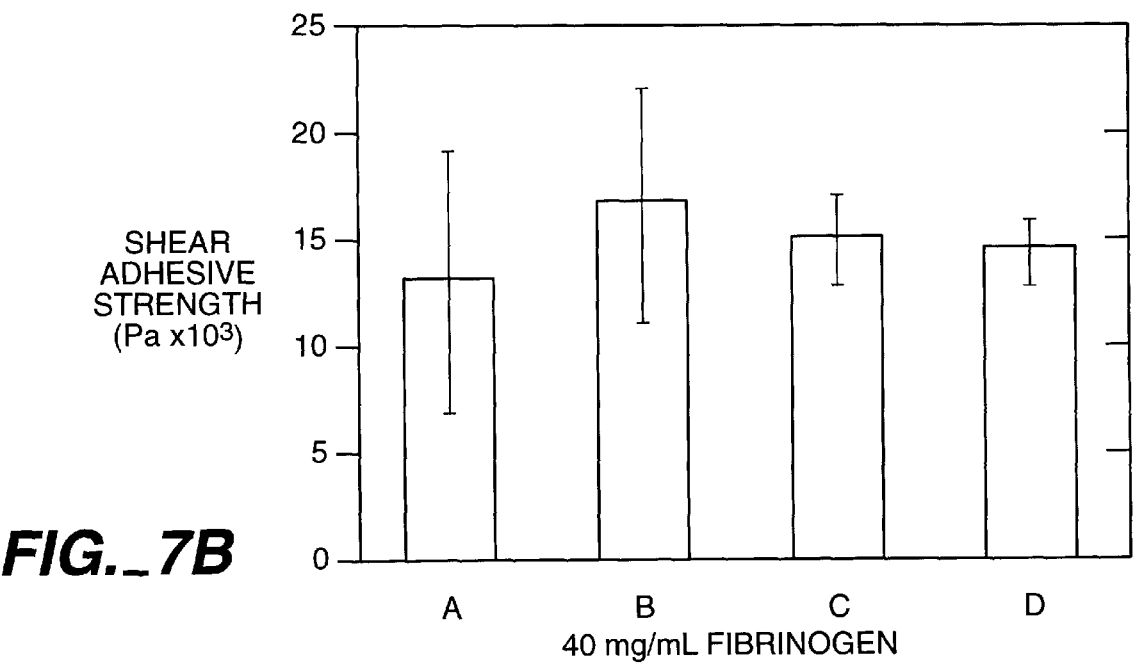
FIG._7B
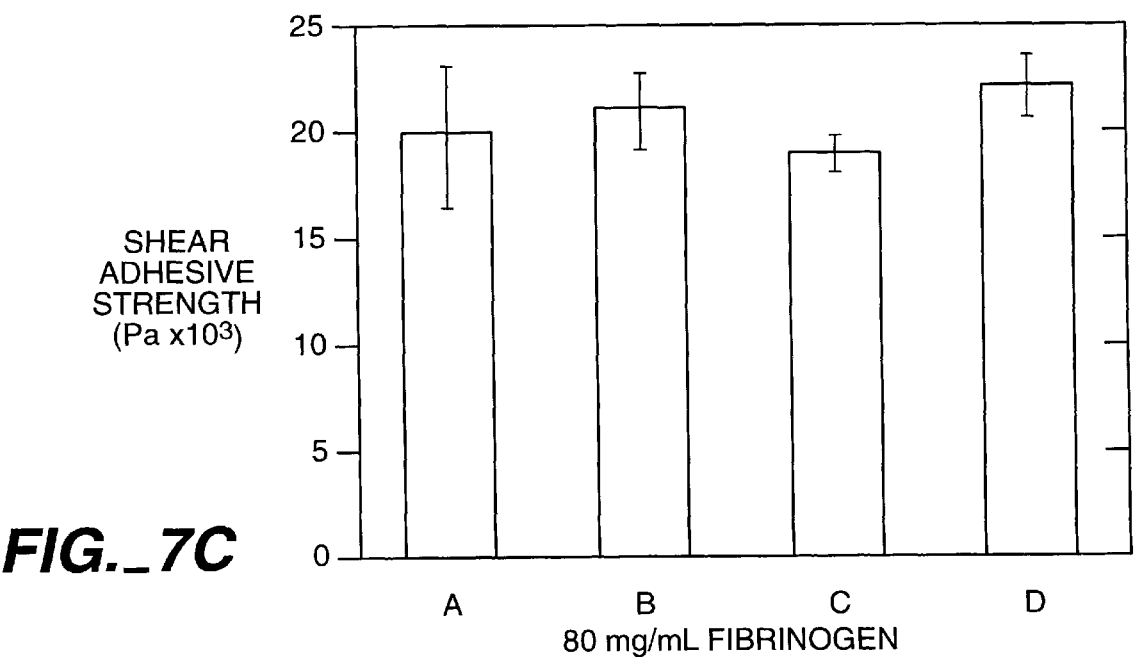
FIG._7C

METHOD AND DEVICE FOR MECHANICAL TESTING OF FIBRIN GLUE STRENGTH

BACKGROUND OF THE INVENTION

1. Field

This invention generally relates to a testing method for evaluating the mechanical properties of a fibrin clot and specifically relates to the use of a polyvinyl chloride (PVC) plastic film as a template for fibrin glue in the mechanical testing.

2. Background

Fibrin glue has been advocated since 1940 (Brennan, 1991). It is widely used in Europe and Japan, and is routinely administered in the U.S. at various centers as an unregulated surgical tissue adhesive (Matras, 1985). Several manufacturers are trying to market a FDA-approved product in the U.S. The benefits of using a tissue adhesive or a tissue sealant like fibrin glue include better patient care, reduced morbidity and mortality, and cost containment (Gibble and Ness, 1990).

Fibrin glue is a three dimensional gel network that results from the enzymatic transformation of soluble fibrinogen by thrombin in the presence of calcium (Marx and Blankenfeld, 1993). The fibrin monomers polymerize and are subsequently cross-linked covalently by activated Factor XIII. The fibrin clot consolidates and adheres to the site of application. The form and structure of fibrin clots are affected by a number of factors which in turn affect the mechanical properties of the fibrin glue (Burnouf-Radosevich, et al. 1990). One of the most important parameters is clot rigidity. Although several papers report the evaluation of shear strength resulting from different fibrinogen concentrations in vitro, a thorough study comparing shear and tensile strength has not been reported. Also, the influence of biochemical and environmental variables has not been previously described in detail.

Studies of fibrin glue have involved measuring the mechanical properties of the fibrin clot. The force required to break the fibrin clot has been used to study the bonding strength of fibrin glue (Duda et al. 1993; Sierra et al. 1992). Tensile strength is force required to break fibrin glue by trans-axial force (applied as the elongating force in the plane of the bond) and shear strength is force required to break fibrin glue along the longitudinal axis (applied parallel to the plane). (See FIG. 2.) The methods used in these studies entail mixing the components of the fibrin glue together and applying the glue between two pieces of substrate material. After the glue solidifies the mechanical properties of the fibrin clot can be tested.

The substrate material typically used in these tests is porcine or other animal skin. There are, however, problems encountered with using porcine (or other animal) skin, such as reproducibility of consistent skin templates, animal source and availability, and storage and stability. Concerns about the humane treatment of animals and minimizing animal testing of products have now lead to the discovery of a practical substitute for the use of porcine skin in the testing of fibrin glue products.

SUMMARY OF THE INVENTION

We have now discovered a method and a device for testing fibrin glue products which do not use skin obtained from animals. In the method, the components of the fibrin glue are applied between two layers of a synthetic substrate material, such as polyvinyl chloride (PVC) film, in a device adapted to measure tensile or shear strengths. When the components have solidified and formed the clot, the force required to separate the layers of the substrate material is measured. Surprisingly, the results obtained using the synthetic polymeric material compared favorably with the use of animal skin.

BRIEF DESCRIPTION OF THE FIGURES

FIG. 1 illustrates a custom made jig used for measuring tensile strength of fibrin glue.

FIG. 2 illustrates the differences between tensile and shear strengths.

FIGS. 3A and 3B compare tensile and shear strengths, respectively, of fibrin glue at varying concentrations on pig skin and PVC strips. The error bars denote standard error with n=4.

FIG. 4 compares tensile and shear strengths using PVC as the fibrin glue template as a function of fibrinogen concentration. The error bars denote standard error with n=4.

FIG. 5 shows the effects of incubation time on shear strength of fibrin glue using 20, 40, and 80 mg/ml of fibrinogen in the presence of 200 units/mil thrombin. The error bars denote standard error with n=4.

FIG. 6 shows the influence of fibrinogen concentration on the shear strength of fibrin glue. The error bars denote standard error with n=6.

FIGS. 7A, 7B, and 7C show shear strength of fibrin glue preparations at 20, 40, and 80 mg/ml fibrinogen, respectively. Comparisons of four lots are shown in each figure. The error bars denote standard error with n=4.

SPECIFIC EMBODIMENTS

Materials and Methods

Bovine thrombin was purchased from Parke-Davis (Morris Plains, N.J.); fresh pig skin was purchased from Pringle Meats Inc. (Oakland, Calif.) and used within 48 hours.

The film used in these experiments was a polyvinyl chloride (PVC) extruded plastic film (Miles-Cutter, Covina, Calif.), although it is anticipated that any plastic film with similar properties would work as well. The film should preferably be from about 7 to about 35 mils thick, and more preferably from about 10 to about 25 mils thick. Functionally, the film should be flexible enough to be easily formed and fitted to the jig on the mechanical testing apparatus. The film should be resistant to stretching such that the measuring of the mechanical properties of the fibrin clot is not interfered with. The film should have surface characteristics (e.g. wettability) which allow it to form a tight bond with the fibrin clot. In a preferred embodiment, the film is embossed with a taffeta finish to provide greater adhesion between the film and the fibrin clot. In more preferred embodiments, the film comprises a material selected from the group consisting of PVC and nylon.

Fibrinogen

Fibrinogen was purified from pooled human plasma. The fibrinogen was freeze-dried and stored at 4° C. until reconstituted with deionized water and warmed to 37° C. before testing. Eight fibrinogen concentrations (10, 20, 30, 40, 50, 60, 70, and 80 mg/mL) were evaluated in this study. The concentration of fibrinogen prior to mechanical testing was determined from the absorbance at 280 nm ($A_{280}$) using a conversion factor of 1% $E_{280}$=15. Clotting time was determined with a MLA ELECTRA 800 Coagulation Analyzer (Pleasantville, N.Y.); the clottability is over 96.1%.

Commercial products of human fibrinogen were Fibrin Sealant (Haemacure Biotech Inc., Canada), Beriplast (Behringwerk AG, Marburg, Germany), and Sigma Chemical Co. (St. Louis, Mo.).

Human thrombin was purified from pooled plasma and reconstituted in 40 mM $CaCl_2$ at a concentration of 200 USP units per mL. The pH was adjusted to 7.5 with 1 N HCL.

Evaluation of Both Tensile and Shear Strength

Tensile strength is defined as the maximum elongating force in the plane of the bond which the adhesive material can withstand without tearing. Shear strength is the maximum force that can be applied parallel to the plane of the adhesive material. Tensile strength measurements were made by cutting fresh pig skin into strips and mounting the strips hair side down onto custom made jigs (see FIG. 1). The test area was 2.5 cm×2.5 cm. The mounted grafts, as well as both fibrinogen and thrombin, were warmed in a 37° C. Ringer's solution bath (Saltz et al., 1991). The skin grafts were joined together by separately applying 0.125 mL of each glue component to the test areas of opposite strips and then applying uniform and light pressure for 5 seconds. The mounted and joined jigs were incubated at time periods ranging from 5 to 90 minutes in a Ringer's solution bath before testing. PVC samples were prepared in a similar manner.

In shear strength measurements, PVC film or pig skin were cut into strips 13 (seen in cross section in FIG. 1) measuring 2.5 cm×5 cm rectangles. Each glue component was separately applied to the one side of the strip measuring 2.5 cm×2.5 cm. Fibrinogen and thrombin were mixed by joining the strips together gently to form fibrin glue clot 15 (seen in cross section in FIG. 1). For both measurements, the strips were separated (FIG. 2) by moving the crosshead of the Instron machine (carrying one strip) away from the fixed clamp (carrying the other strip). The Instron 1130 mechanical testing machine (Canton, Mass.) was operated at a constant speed of 5 cm/minute using a 2 Kg load cell. The maximum breaking strength (tensile strength) of the fibrin glue were measured in grams per 6.25 $cm^2$. The results were expressed in Pascal. The force was recorded as a load-extension curve and the highest force achieved was used as the maximum breaking strength. All samples for each tested group were prepared on the day of experiment.

EXAMPLE 1

Comparison between PVC and pig skin

In the first series of experiments, we compared tensile and shear strength of fibrin glue using fresh pig skin and PVC film as templates. The results (FIG. 3A) show the tensile strength measured at a three fibrinogen concentrations (20, 40, and 80 mg/mL). There were no significant differences observed between pig skin and PVC. For the shear strength measurement (FIG. 3B), 3–4 fold higher values with PVC were observed than with pig skin at the lowest fibrinogen concentrations (20 mg/mL). At the highest fibrinogen concentration tested (80 mg/mL), both templates demonstrated similar breaking strengths. In each experiment, the thrombin component contained 200 IU/ml thrombin and 40 mM $CaCl_2$.

EXAMPLE 2

Comparison of tensile versus shear strength on PVC

Fibrin glue was made with 20, 40, and 80 mg/ml fibrinogen and 200 IU/ml thrombin containing 40 mM $CaCl_2$ as described in the materials and methods section. The shear strength values for PVC were about 2-fold greater than the tensile strength values (FIG. 4). Increased fibrinogen concentration correlated with an increase in shear strength.

EXAMPLE 3

Time course of glue strength

In order to determine the minimum time required to establish the maximum attainable glue strength of fibrin glue, shear strength of fibrin glue as a function of different fibrinogen concentration and incubation time was investigated. Fibrin glue was prepared at 20, 40, and 80 mg/ml fibrinogen and 200 IU/ml thrombin containing 40 mM $CaCl_2$ on PVC templates as described in the materials and methods section and incubated at room temperature for different time intervals. The results shown in FIG. 5 suggest that a 30 minute incubation was sufficient to obtain the maximum strength at fibrinogen concentrations of 20 or 40 mg/mL. When a higher concentration of fibrinogen was employed, the time necessary to achieve maximum shear strength decreased to less than 5 minutes (earliest point tested). These results and the results following confirm literature observations that fibrinogen concentration is an important parameter for obtaining an effective fibrin glue adhesive.

EXAMPLE 4

Influence of fibrinogen concentration

To further characterize the effect of concentration of fibrinogen on the adhesive properties of fibrin glue, shear strength measurements were determined as a function of fibrinogen concentration. Fibrin glue was prepared using different fibrinogen concentrations (10–80 mg/mL) and 200 IU/ml thrombin containing 40 mM $CaCl_2$ on PVC templates. As shown in FIG. 6, the shear strength was dependent on the concentration of fibrinogen employed. There was a sharp increase in shear strength with increasing fibrinogen concentration.

EXAMPLE 5

Lot to lot comparison

The comparison of shear strength in different purification lots is shown FIG. 7. Four separate lots of fibrinogen were used to prepare fibrin glue at different fibrinogen concentrations (20, 40 and 80 mg/mL) as described in the materials and methods section using PVC templates. The strength evaluations were performed using identical conditions for comparison. The different lots were compared at three fibrinogen concentrations. No significant difference in shear adhesive strength was found for these lots at any given fibrinogen concentration.

EXAMPLE 6

Comparison of commercial products with freshly isolated fibrin glue

The shear strengths of three commercial fibrinogen products (Haemacure, Beriplast, and Sigma Chemical Co.) was compared with that of fibrin glue which was freshly isolated from pooled human plasma. The shear strength of each of the different preparations was compared at 20, 40, and 80 mg/mL fibrinogen concentrations. The results are shown in Table I. No significant differences were observed between the freshly isolated fibrin glue preparations (Bayer) and the Beriplast fibrin glue at all three fibrinogen concentrations. The Sigma product exhibited lower values than the Bayer and Beriplast preparation. The Haemacure product had significantly lower shear strength than the Bayer preparation and other commercial products.

TABLE I

Comparison of shear strengths of products from various sources using PVC film

| Sources | Fibrinogen Conc. (mg/ml) | Incubation time (hours) | Thrombin source (200 U/ml in 40 mM $Ca^{++}$) | Shear Strength Pa (±SE) |
|---|---|---|---|---|
| Bayer | 20 | 2 | Bayer | 11,312 (3440) |
|  | 40 | 2 |  | 16,688 (5440) |
|  | 80 | 2 |  | 21,008 (1664) |
| Hemaseel | 20 | 2 | Hemaseel | 1392 (128) |
| (Fibrin Sealant) | 40 | 2 |  | 3408 (592) |
|  | 80 | 2 |  | 4272 (400) |
| Beriplast | 20 | 2 | Parke-Davis | 6656 (3824) |
|  | 40 | 2 |  | 10,000 (1600) |
|  | 80 | 2 |  | 17,664 (3024) |
| Sigma | 20 | 2 | Bayer | 3440 (496) |
|  | 40 | 2 |  | 7360 (1376) |
|  | 80 | 2 |  | 14,400 (7168) |

EXAMPLE 7
Influence of temperature

Investigation of the effect of temperature on fibrin glue is important because certain applications require that the product be used at surgical body temperatures of 30–35° C. These applications include the use of fibrin glue during surgical operations such as open-heart surgery and liver transplantation. We evaluated the mechanical strength of fibrin glue at 21° C. and 37° C. following incubation times of at least 2 hours. As shown in Table II, there were no significant differences in shear strength measurements of fibrin glue at 20, 40, and 80 mg/mL of fibrinogen for either 21° C. or 37° C.

mechanical strength of fibrin glue has been assessed and several conclusions may be made.

First, incubation temperature did not play an important role in the mechanical strength of fibrin glue. The data demonstrated no significant difference at 21° C. and 37° C.

Next, maximum mechanical strength of fibrin glue was both time and concentration dependent. At 20 and 40 mg/ml fibrinogen, maximum strength was achieved after a 30 minute incubation. At 80 mg/ml fibrinogen, maximum strength was achieved during a five minute incubation. The higher strength is obtained at higher fibrinogen concentration. The results confirm literature observations that fibrinogen concentration is important for obtaining an effective

TABLE II

Effects of source and temperature

| Fibrinogen Conc. (mg/ml) | Thrombin source (200 U/ml in 40 mM $Ca^{++}$) | Template | Shear Strength (Pa (±SE)) | |
|---|---|---|---|---|
|  |  |  | at 21° C. | at 37° C. |
| 20 | Bayer | PVC film | 8944 (3152) | 10,928 (800) |
| 40 | Bayer | PVC film | 17,808 (4784) | 11,968 (3488) |
| 80 | Bayer | PVC film | 22,560 (3440) | 18,656 (3264) |
| 40 | Parke-Davis | PVC film | 21,440 (4160) | * |
| 80 | Parke-Davis | PVC film | 22,880 (5552) | * |
| 40 | Bayer | Pig Skin | 14,848 (6832) | * |
| 80 | Bayer | Pig Skin | 20,000 (6800) | * |

*not determined

EXAMPLE 8
Thrombin source

The mechanical strength of fibrin glue was also shown to be independent of thrombin source [human and porcine (Parke-Davis)], as shown in Table II.

DISCUSSION

Measurement of mechanical strength or breaking strength of fibrin glue is an important parameter for testing the resiliency of this bioadhesive in vitro. We show that a synthetic polymeric substrate such as PVC can be utilized as a convenient, well-defined template for mechanical strength measurement of fibrin glue instead of pig skin. It can be used to measure both shear and tensile strength properties of fibrin glue with high reproducibility. This testing method allows more consistent performance of the fibrin glue analysis, and could be used for product quality control. Analysis of biological and environmental variables on the fibrin glue adhesive. There is no standard existing for a minimum acceptable breaking strength value.

In conclusion, mechanical strength measurement provides a way to measure the rigidity of the fibrin clot. Our study indicates that the testing method is sensitive to the fibrinogen source and is useful for investigating the variables for an optimal formulation of fibrin glue.

The above examples are intended to illustrate the invention and it is thought variations will occur to those skilled in the art. For example, it is thought that other synthetic polymeric substrate materials (e.g. plastic films with similar surface properties to PVC films) can be used as well as the PVC of the working examples. Accordingly, it is intended that the scope of the invention should be limited only by the claims below.

REFERENCES

Brennan, M., Fibrin Glue, Blood Reviews 5: 240–44 (1991).
Burnouf-Radosevich, M., et al., Biochemical and physical properties of a solvent-detergent-treated fibrin glue, Vox Sang. 58: 77–84 (1990).

Duda, G. N., et al., Testing method for mechanical properties of fibrin glue, J. Appl. Biomater. 4: 341–46 (1993).

Gibble, J. W., and Ness, P. M, Fibrin glue: the perfect operative sealant, Transfusion 30: 741–47 (1990).

Lerner, R., and Binur, N. S, Current research review: Current status of surgical adhesives, J. Surg. Res. 48: 165–181 (1990).

Matras, H., Fibrin seal: the state of the art, J. Oral Maxillofac. Surg. 43: 605–11 (1985).

Marx, G., and Blankenfeld, A., Kinetic and mechanical parameters of pure and cryoprecipitate fibrin, Blood Coagul. and Fibrinolysis 4: 73–78 (1993).

Saltz, R., et al., Experimental and clinical applications of fibrin glue. Plast. Reconstr. Surg. 88: 1005–1015 (1991).

Sierra, D. H., et al., A method to determine shear adhesive strength of fibrin sealants. J. Appl. Biomater. 3: 147–51 (1992).

What is claimed is:

1. In a method of testing the strength of a fibrin clot comprising the steps of forming a fibrin clot between a first substrate material and a second substrate material, wherein at least one of said first and second substrate materials comprises animal skin, and measuring the force required to separate the first substrate material from the second substrate material, the improvement wherein the animal skin is replaced with a substrate which comprises polyvinyl chloride, wherein the tensile strength of the fibrin clot as measured using the polyvinyl chloride film is substantially similar in magnitude to the tensile strength of the fibrin clot as measured using animal skin.

2. In a device for measuring tensile strength of a glue and comprising opposing surfaces each having affixed thereto samples of an animal skin adapted to receive a glue sample and then be pulled apart under conditions which permit measurement of the force needed to pull the surfaces freely apart, the improvement which comprises a polyvinyl chloride film as a replacement for the animal skin, wherein the tensile strength of the glue as measured using the polyvinyl chloride film is substantially similar in magnitude to the tensile strength of the glue as measured using animal skin.

* * * * *